(12) United States Patent
Lo

(10) Patent No.: US 10,024,782 B2
(45) Date of Patent: Jul. 17, 2018

(54) SMOKE CHAMBER AND SMOKE DETECTOR USING THE SAME

(71) Applicant: NANNING FUGUI PRECISION INDUSTRIAL CO., LTD., Nanning (CN)

(72) Inventor: Wu-Jen Lo, New Taipei (TW)

(73) Assignee: NANNING FUGUI PRECISION INDUSTRIAL CO., LTD., Nanning (CN)

( * ) Notice: Subject to any disclaimer, the term of this patent is extended or adjusted under 35 U.S.C. 154(b) by 0 days.

(21) Appl. No.: 15/379,711

(22) Filed: Dec. 15, 2016

(65) Prior Publication Data

US 2018/0149581 A1    May 31, 2018

(30) Foreign Application Priority Data

Nov. 25, 2016 (TW) .............................. 105138955 A (51) Int. Cl.
| | |
|---|---|
| *G01N 21/00* | (2006.01) |
| *G01N 21/03* | (2006.01) |
| *G01N 21/53* | (2006.01) |
| *G08B 17/107* | (2006.01) |

(52) U.S. Cl.
CPC ......... *G01N 21/0303* (2013.01); *G01N 21/53* (2013.01); *G08B 17/107* (2013.01); *G01N 2201/022* (2013.01); *G01N 2201/068* (2013.01)

(58) Field of Classification Search
CPC ...... G08B 17/07; G08B 17/10; G08B 17/103; G08B 17/107; G01N 21/0303; G01N 21/53

USPC ......... 340/628, 630, 693.5, 693.12; 250/574, 250/575; 356/338, 438
See application file for complete search history.

(56) References Cited

U.S. PATENT DOCUMENTS

| | | | | |
|---|---|---|---|---|
| 4,897,634 | A * | 1/1990 | Sawa ................... | G08B 17/107 174/377 |
| 5,587,790 | A * | 12/1996 | Nagashima .......... | G08B 17/107 250/574 |
| 6,300,876 | B1 | 10/2001 | Sakura et al. | |
| 6,756,905 | B2 * | 6/2004 | Rattman .............. | G08B 17/107 250/574 |
| 6,778,091 | B2 | 8/2004 | Qualey, III et al. | |
| 8,201,973 | B2 * | 6/2012 | Kudoh .................. | G08B 29/08 362/253 |
| 2008/0218364 | A1 | 9/2008 | Mizuo | |
| 2008/0246623 | A1* | 10/2008 | Nagashima ............ | G01N 21/21 340/630 |

FOREIGN PATENT DOCUMENTS

TW        I235965        7/2005

* cited by examiner

*Primary Examiner* — Hung T Nguyen
(74) *Attorney, Agent, or Firm* — ScienBiziP, P.C.

(57) ABSTRACT

A smoke detecting enclosure which is impervious to interference from outside light sources includes a smoke detecting housing and an upper cover. The smoke detecting housing has an receiving space with openings on one side, an opposite side defines two opposite installation parts carrying a light emitter and a light receiver. A peripheral surface of the smoke detecting housing is a first terraced wall and the upper cover when coupled with the opening comprises an open-ended cavity and a light barrier. The light barrier is opposite to the opening and is on an open path to the opening. A smoke detector is further disclosed.

18 Claims, 11 Drawing Sheets

SMOKE CHAMBER AND SMOKE DETECTOR USING THE SAME

FIELD

The subject matter herein generally relates to a smoke chamber and smoke detectors using the smoke chamber.

BACKGROUND

In a typical smoke detector system there is a smoke-detecting chamber, within the chamber there is a light source with a light beam and a light sensor. The light sensor detects light scattered from the light beam by smoke particles within the chamber. When a predetermined smoke level is exceeded, an alarm signal is produced. In smoke detector systems, extraneous light may come into the smoke chamber and cause false alarms.

BRIEF DESCRIPTION OF THE DRAWINGS

Implementations of the present technology will now be described, by way of example only, with reference to the attached figures.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein can be practiced without these specific details. In other instances, methods, procedures, and components have not been described in detail so as not to obscure the related relevant feature being described. The drawings are not necessarily to scale and the proportions of certain parts may be exaggerated to better illustrate details and features. The description is not to be considered as limiting the scope of the exemplary embodiments described herein.

Several definitions that apply throughout this disclosure will now be presented.

The term "substantially" is defined to be essentially conforming to the particular dimension, shape, or other feature that the term modifies, such that the component need not be exact. For example, "substantially cylindrical" means that the object resembles a cylinder, but can have one or more deviations from a true cylinder. The term "comprising" means "including, but not necessarily limited to"; it specifically indicates open-ended inclusion or membership in a so-described combination, group, series and the like.

Figure 1:
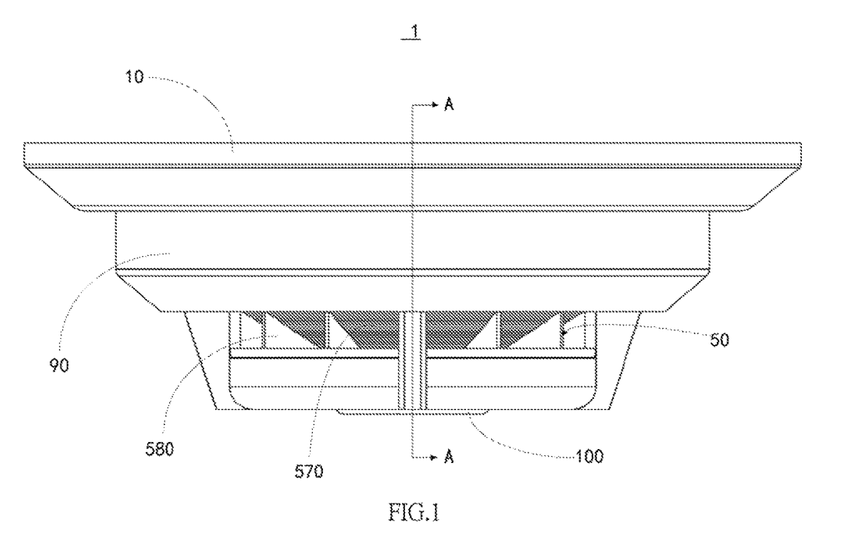
FIG. 1 is an isometric view of an exemplary embodiment of a smoke detector.
Figure 2:
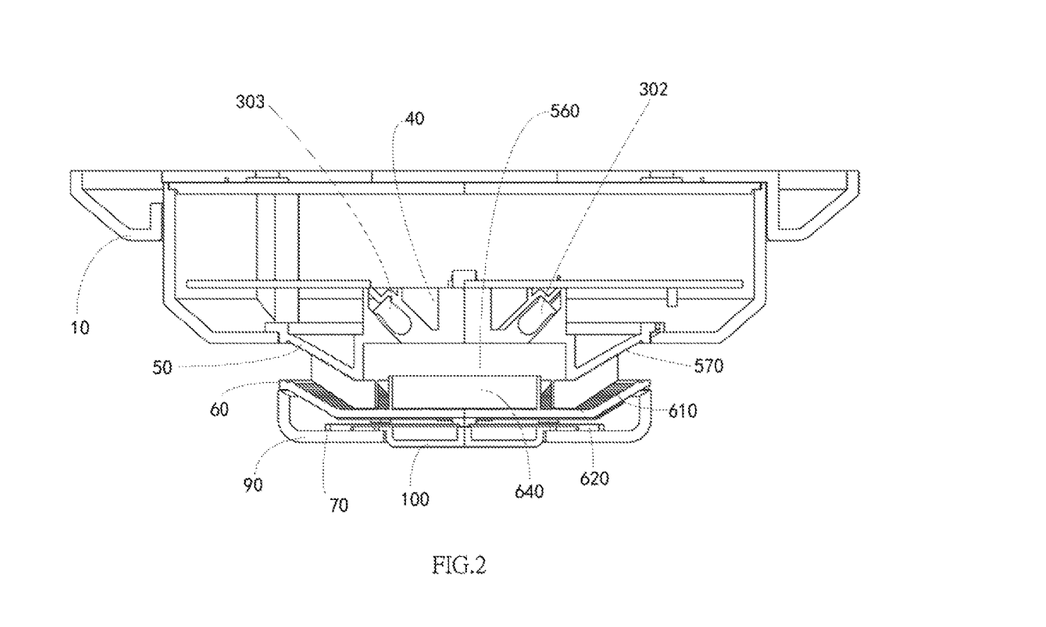
FIG. 2 is a cross sectional view along line A-A of the smoke detector of FIG. 1.
Figure 3:
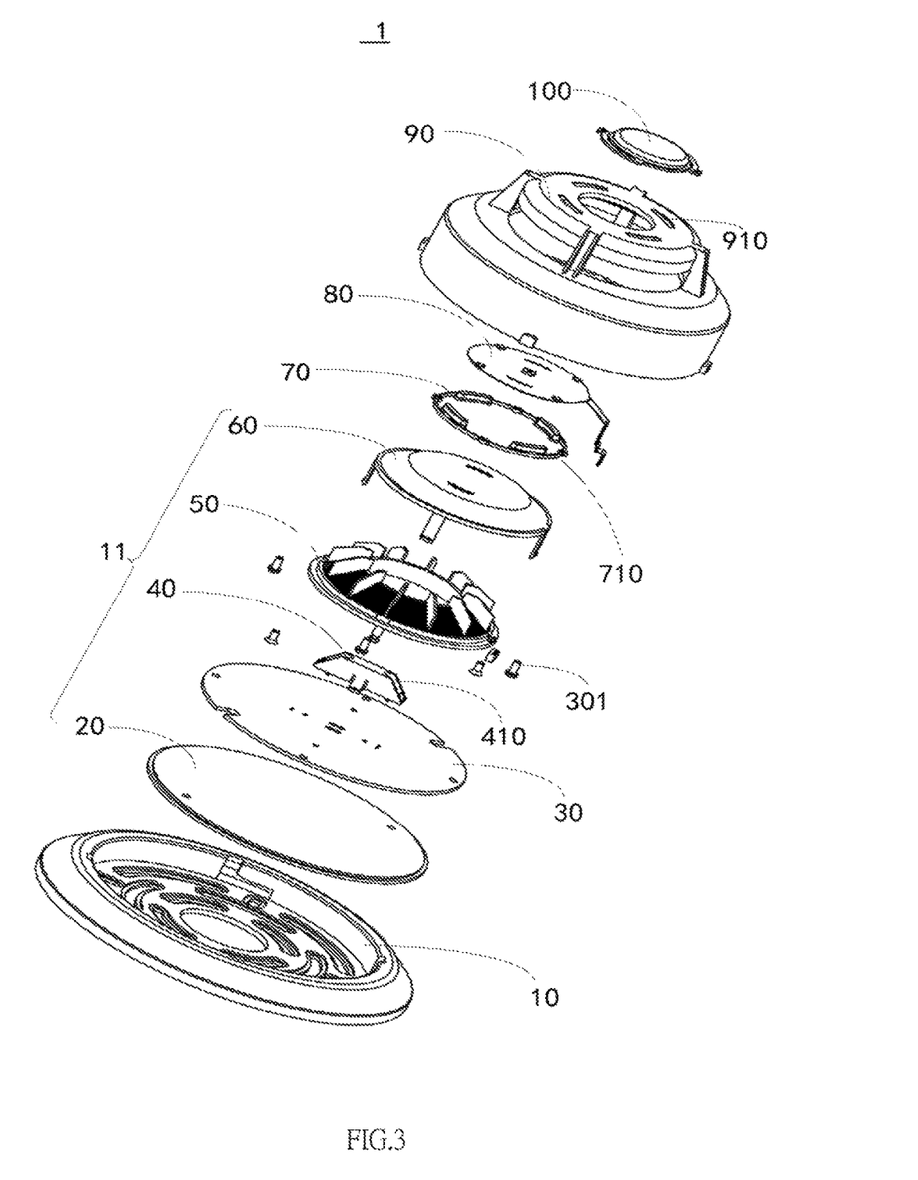
FIG. 3 is an exploded view of the smoke detector of FIG. 1.

FIGS. 1 to 3 illustrate a smoke detector 1 in an exemplary embodiment.

The smoke detector 1 can include a chassis 10 and an enclosure 90 mounted to the chassis 10. A smoke chamber 11, a circuit board 30, a light emitter 302 and a light receiver 303 can be received in the enclosure 90. The enclosure 90 defines a plurality of smoke entrances 950. In case of fire, smoke can get into the smoke chamber 11 through the smoke entrances 950. The light emitter 302 and the light receiver 303 are electrically connected to the circuit board 30. An angle between optical axis of the light emitter 302 and optical axis of the light receiver 303 can be preset as an obtuse angle. It is understood that the angle between optical axis of the light emitter 302 and optical axis of the light receiver 303 can also be preset as an acute angle, so long as optical axis of the light emitter 302 and optical axis of the light receiver 303 are non-collinear.

The smoke chamber 11 can include a smoke detecting housing 50, a bottom plate 20, and an upper cover 60. The smoke chamber 11 can include two opposite ends enclosed by the bottom plate 20 and the upper cover 60. The circuit board 30 can be fixed to the smoke detecting housing 50 by fastener 40 and screws 301.

Figure 4:
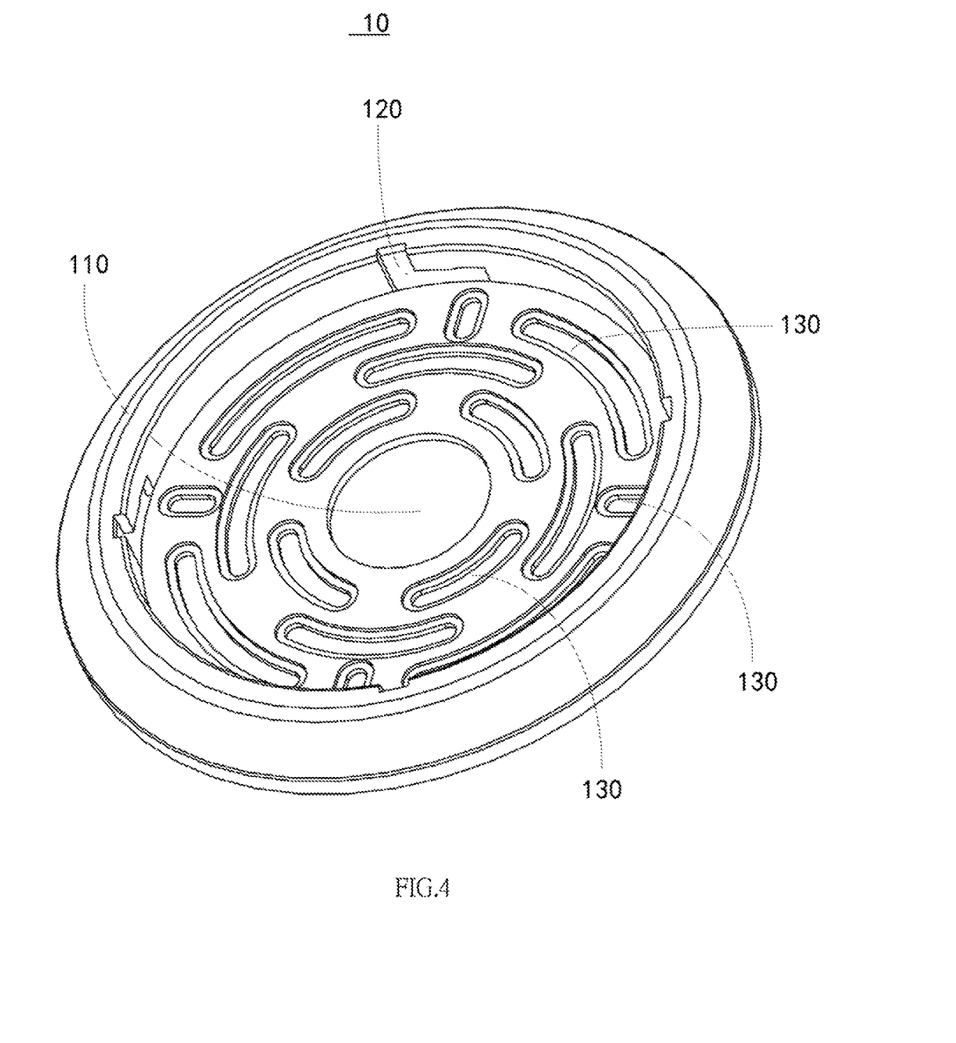
FIG. 4 is an isometric view of the chassis of the smoke detector of FIG. 3.

Referring to FIG. 4, the chassis 10 includes a cable hole 110, a plurality of mounting holes 130, and snap joints 120. Cables of the circuit board 30 can exit the enclosure 90 through the cable hole 110.

Figure 5:
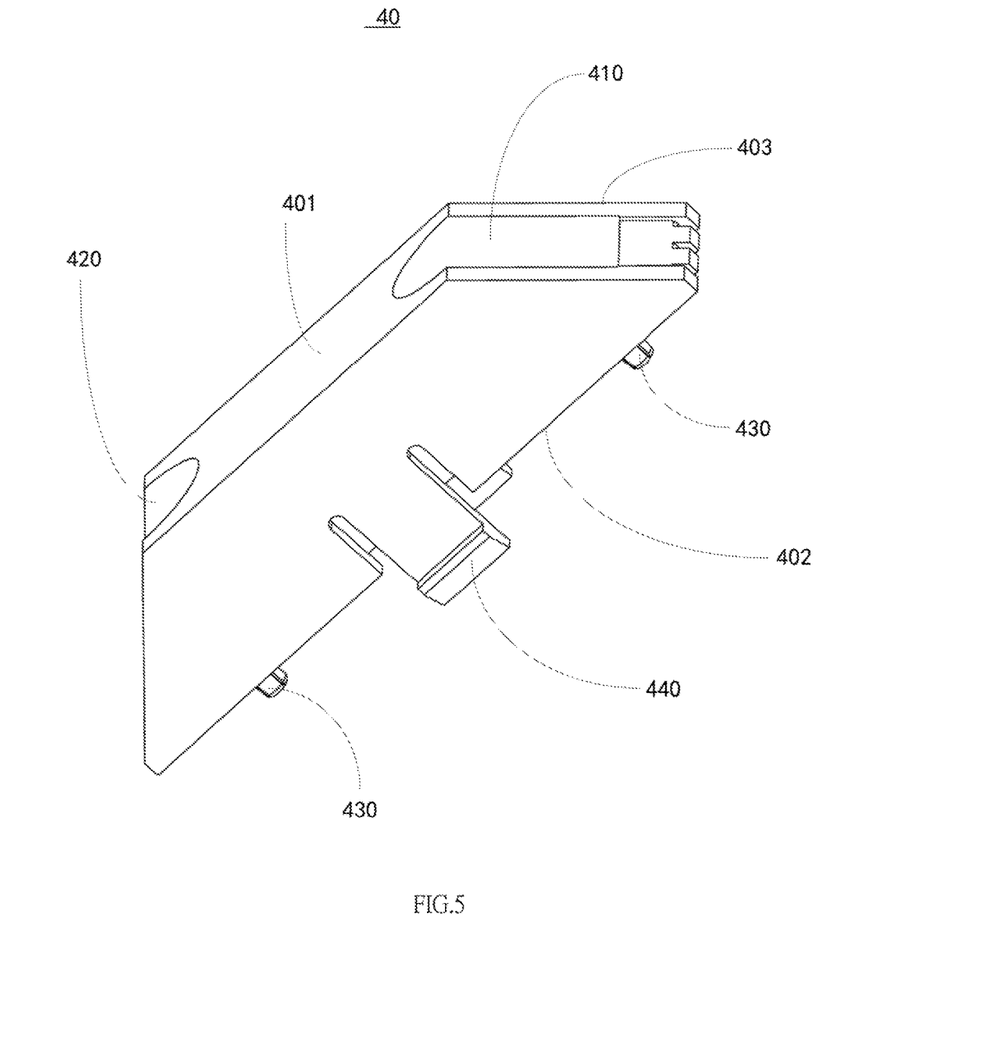
FIG. 5 is an isometric view of the fixture of the smoke detector of FIG. 3.

Referring to FIG. 5, the fastener 40 can include a first plane 401, a second plane 402 opposite to the first plane 401, two side planes (not shown) connected between the first plane 401 and the second plane 402, and two opposite bevel planes 403 connected between the first plane 401 and the second plane 402. One of the two opposite bevel planes 403 defines a first light emitter bearing surface 410, the other one of the two opposite bevel planes 403 defines a first light receiver bearing surface 420. An angle between the two opposite bevel planes 403 is the same as the angle between optical axis of the light emitter 302 and optical axis of the light receiver 303. The first plane 401 is fixed to the smoke detecting housing 50 and the second plane 402 is fixed to the circuit board 30. Each of the two side planes can define a first hook 440 extending towards the second plane 402. At least two locating pillars 430 can be defined on the second plane 402, the locating pillars 430 are coupled with locating holes (not shown) preset on the circuit board, to mount the circuit board 30 to a predetermined position.

Figure 6:
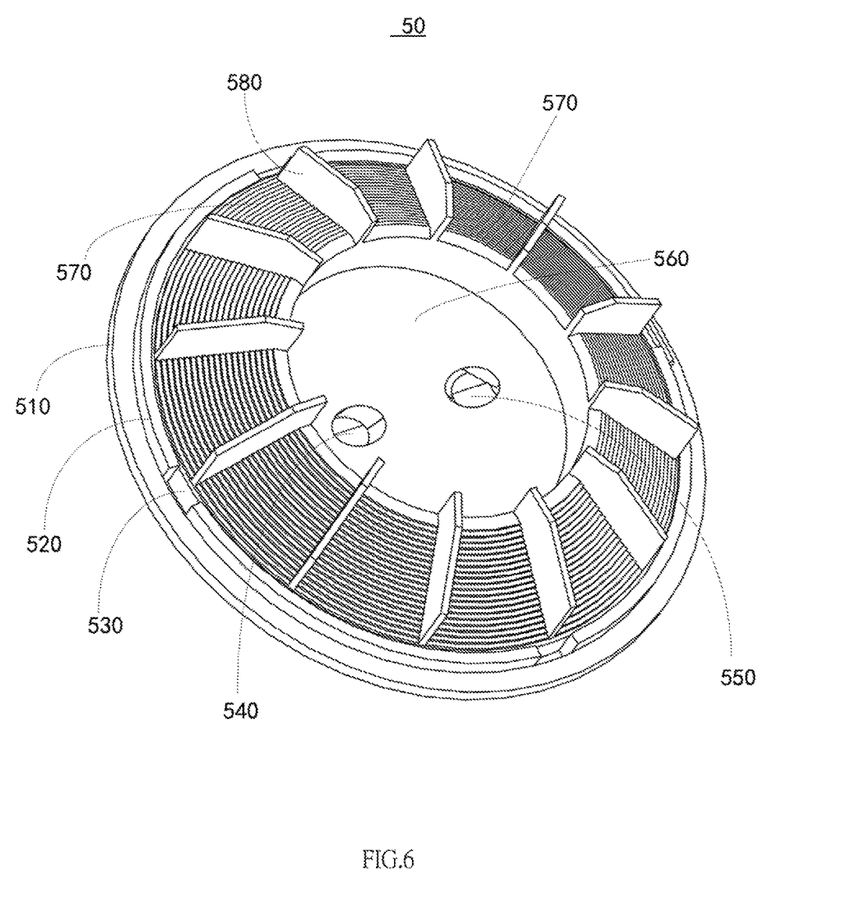
FIG. 6 is an isometric view of the smoke detecting housing of the smoke detector of FIG. 3.
Figure 7:
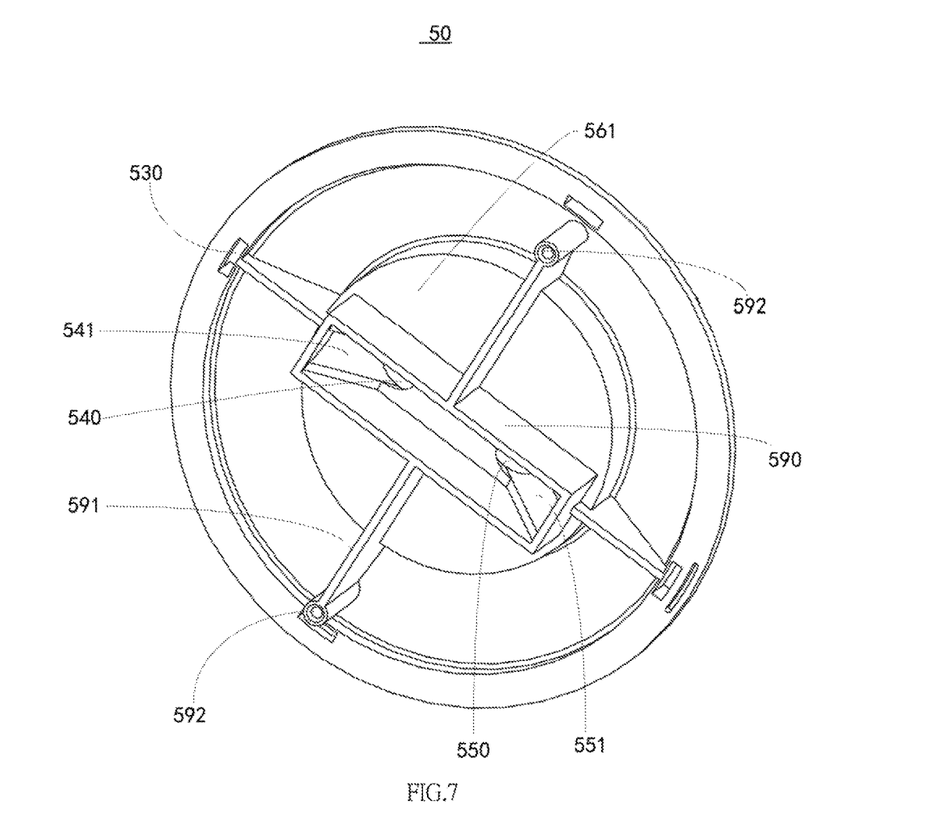
FIG. 7 is an isometric view of the smoke detecting housing of FIG. 6 seen from another perspective.

Referring to FIGS. 6 and 7, the smoke detecting housing 50 defines an receiving space 560 inside. The receiving space 560 is divided into two parts by a joint plate 561. One part of the receiving space 560 defines an opening (not labeled), the other part of the receiving space 560 defines a lens hood 590. The lens hood 590 defines a second light emitter bearing surface 541 and a second light receiver bearing surface 551. The second light emitter bearing surface 541 together with the first light emitter bearing surface 410 form an installation part for the light emitter 302. The second light receiver bearing surface 551 together with the first light receiver bearing surface 420 form an installation part for the light receiver 303. An emitting hole 540 and a receiving hole 550 are defined in the joint plate of the receiving space 560. The emitting hole 540 is connected to the installation part of the light emitter 302 for light emitted by the light emitter 302 to pass through the emitting hole 540 into the receiving space 560. The receiving hole 550 is connected to the installation part of the light receiver 303 for scattered light to pass through the receiving hole 550 and be received by the light receiver 303.

A peripheral surface of the smoke detecting housing 50 can be a first terraced wall 570. Light, together with smoke particles, can pass through the smoke entrances 950 (shown in FIG. 10) into the receiving space 560. The first terraced wall 570 will reflect most of light in the detecting housing 50 from outside sources, by which means interference by outside light on the light receiver 303 is suppressed or prevented.

The smoke detecting housing 50 can define an annular plate 510. The smoke detecting housing 50 can be mounted to the enclosure 90 through the annular plate 510. A plurality of connecting gaps 530 can be defined on the annular plate 510 to fix the upper cover 60 to the smoke detecting housing 50. A plurality of supporting plates 580 can be defined on the first terraced wall 570. The upper cover 60 can be fixed to the smoke detecting housing 50 and be supported by the supporting plates 580. The annular plate 510 can define a pad 530 on which an insect-proof net (not shown) can be mounted.

The lens hood 590 can define at least two installation members 591. Screw holes 592 can be defined on the installation member 591 so that the circuit board 30 can be fixed to the smoke detecting housing 50 by screws.

Figure 8:
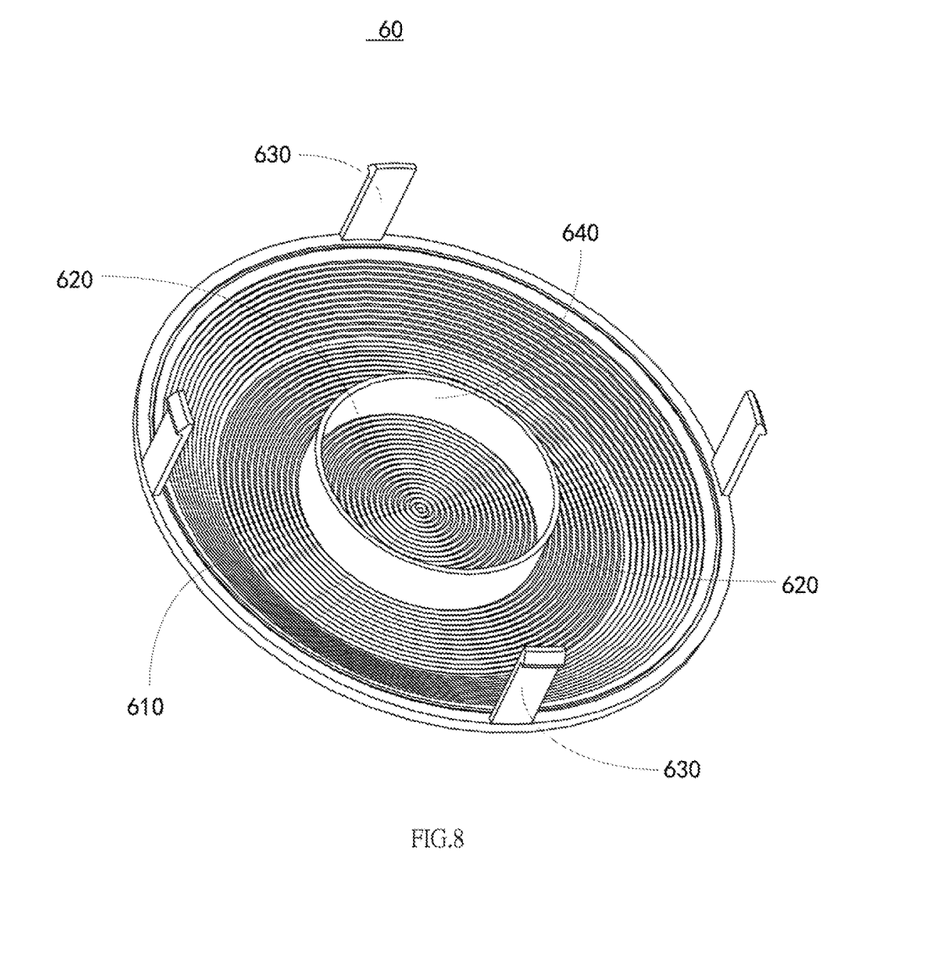
FIG. 8 is an isometric view of the upper cover of the smoke detector of FIG. 3.
Figure 9:
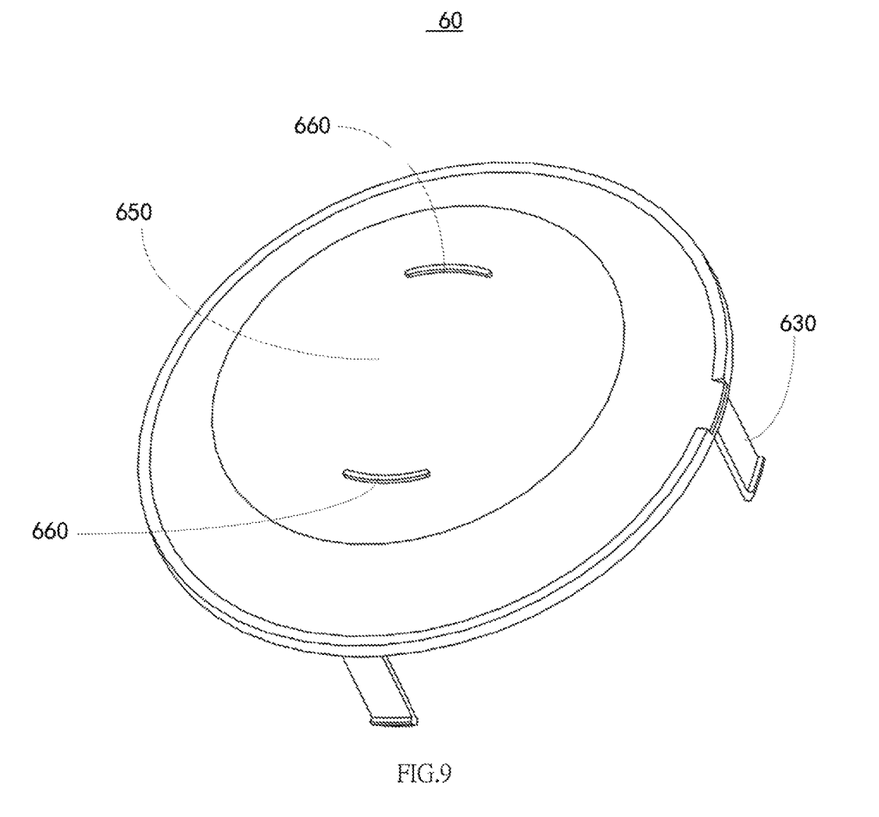
FIG. 9 is an isometric view of upper cover of FIG. 8 seen from another perspective.
Figure 11:
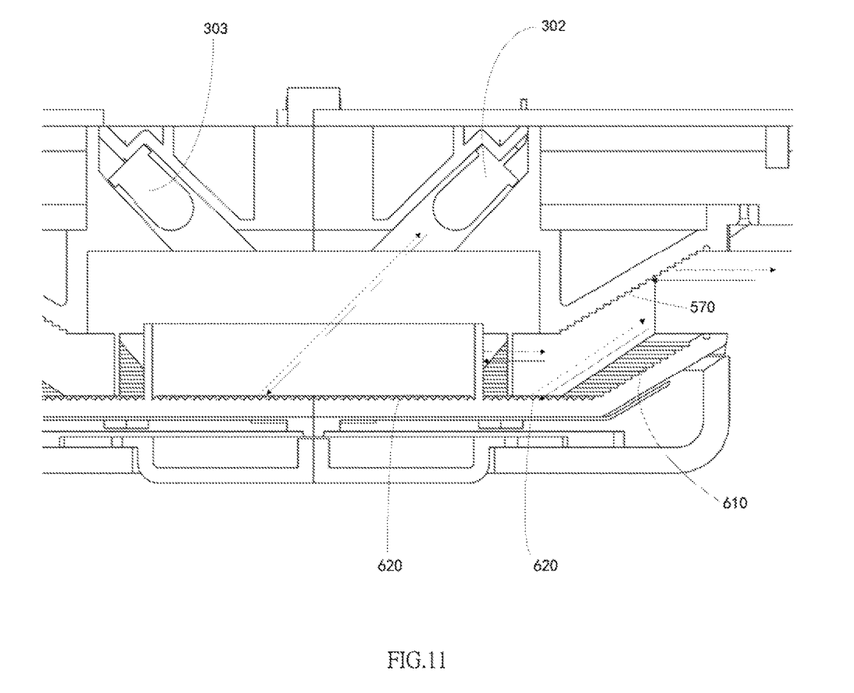
FIG. 11 is working principles diagram of the smoke detector of the smoke detector of FIG. 2.

Referring to FIGS. 8, 9, and 11, the upper cover 60 can include a cavity (not labeled) with one open end and a light barrier 640 therein. The light barrier 640 is opposite to the open end and located on an open path to the open end. A free end of the light barrier 640 is parallel with the end surface of the opening, and a projection of the light barrier 640 on the receiving space 560 is within the receiving space 560.

In at least one exemplary embodiment, an inner surface of the upper cover 60 includes a second terraced wall 610. The second terraced wall 610 is opposite to the first terraced wall 570 and parallel with the first terraced wall 570. The upper cover can include a cover plate (not labeled) and a flange (not labeled) extending from the edge of the cover plate. The flange is parallel to the first terraced wall 570 and the second terraced wall 610 is formed on an inner side of the flange. A peripheral surface of the flange is flush with an end surface of the opening.

The upper cover 60 can further include a zigzag structure 620 in the cavity, the zigzag structure 620 is opposite to the installation part for the light emitter 302. In the absence of smoke, light emitted by the light emitter 302 is reflected along the emitting direction and is not received by the light receiver 303. Thus, a false alarm can be avoided when the light emitter 302 emits light by mistake.

Figure 10:
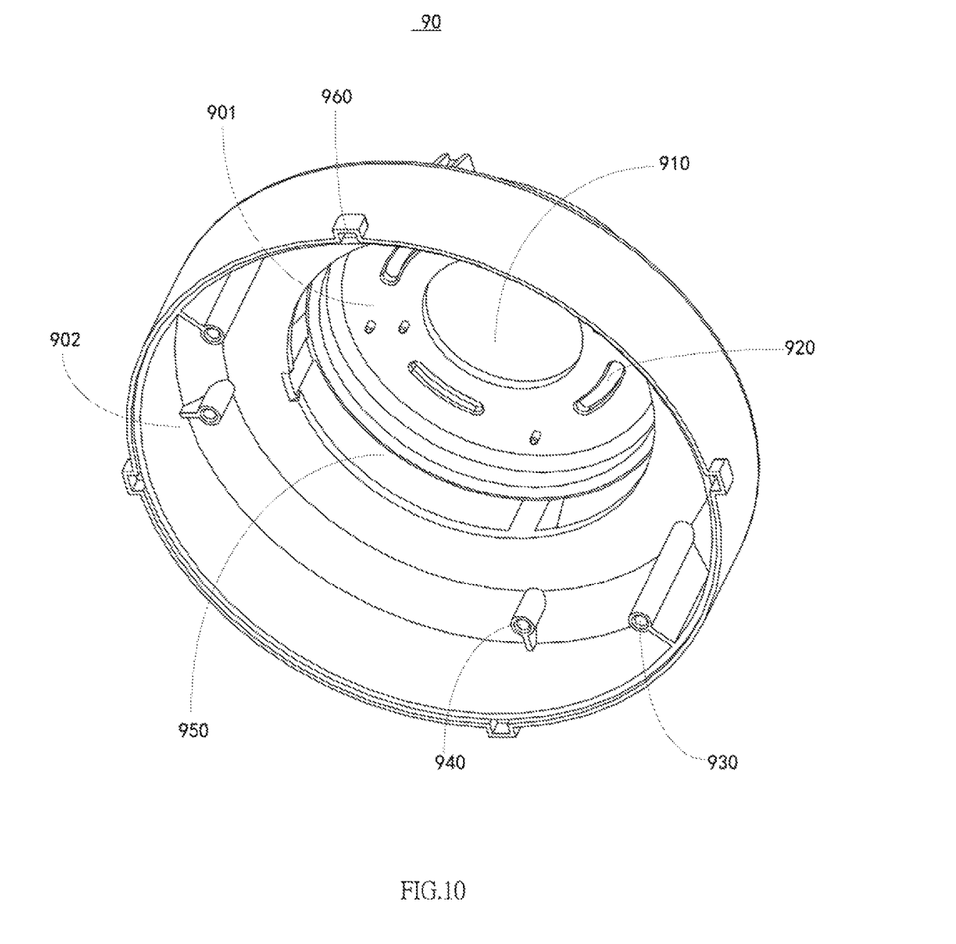
FIG. 10 is an isometric view of the enclosure of the smoke detector of FIG. 3.

Referring to FIG. 10, the enclosure 90 can include a first installation room 901 and a second installation room 902 connected to the first installation room 901 in a ladder-pattern. The smoke entrances 950 are defined between the first installation room 901 and the second installation room 902. Screw holes 930, 940 can be defined in the second installation room 902 to fix the bottom plate 20 and the circuit board 30. The second installation room 902 defines latches 960 coupled with the snap joint 120.

Referring back to FIGS. 3 and 10, the smoke detector 1 can further include a testing unit, an alarm unit, and an operating unit accommodated in the enclosure 90. The testing unit can include a flexible printed circuit board (FPC) 80, testing parts connected to the FPC 80, and a testing button 100. The alarm unit can include a light belt 70 with a plurality of alarm lights 710. The alarm lights 710 can be different in color to show smoke density or working states of the smoke detector 1. Accordingly, the enclosure 90 includes a button hole 910 and a plurality of light holes 920.

The embodiments shown and described above are only examples. Even though numerous characteristics and advantages of the present technology have been set forth in the foregoing description, together with details of the structure and function of the present disclosure, the disclosure is illustrative only, and changes may be made in the details, including matters of shape, size, and arrangement of the parts within the principles of the present disclosure, up to and including the full extent established by the broad general meaning of the terms used in the claims.

What is claimed is:

1. A smoke chamber comprising:
a smoke detecting housing having an receiving space; an opening defined at a side of the receiving space, an opposite side of the receiving space defines two installation parts facing to each other for a light emitter and a light receiver; a peripheral surface of the smoke detecting housing defines a first terraced wall; and
an upper cover coupled with the opening, the upper cover comprising a cavity with an open end and a light barrier positioned in the cavity;
wherein the light barrier is facing towards the opening and forms a path between the light barrier and the opening.

2. The smoke chamber of claim 1, wherein a free end of the light barrier is parallel to an end surface of the opening.

3. The smoke chamber of claim 1, wherein a projection of the light barrier on the receiving space locates within the receiving space.

4. The smoke chamber of claim 1, wherein an inner surface of the upper cover comprises a second terraced wall opposite to the first terraced wall.

5. The smoke chamber of claim 4, wherein the upper cover comprises a cover plate and a flange extending from an edge of the cover plate, the flange is parallel to the first terraced wall.

6. The smoke chamber of claim 4, wherein a peripheral surface of the flange is flush with an end surface of the opening.

7. The smoke chamber of claim 1, wherein the upper cover comprises a zigzag structure in the cavity, the zigzag structure is facing towards the installation part for the light emitter.

8. The smoke chamber of claim 1, wherein the smoke chamber further comprises a base plate and a fastener connected between the base plate and the smoke detecting housing, the fastener comprises a first light emitter bearing surface and a first light receiver bearing surface, the smoke detecting housing comprises a second light emitter bearing surface coupling with the first light emitter bearing surface and a second light receiver bearing surface coupling with the first light receiver bearing surface.

9. A smoke detector comprising:
a chassis;
an enclosure mounted to the chassis;
a circuit board with at least one light emitter and one light receiver received in the enclosure; and
a smoke detecting housing in the enclosure, the smoke detecting housing comprising:

an receiving space; an opening is defined at a side of the receiving space, an opposite side of the receiving space defines two installation parts facing to each other for a light emitter and a light receiver; a peripheral surface of the smoke detecting housing defines a first terraced wall; and an upper cover coupled with the opening, the upper cover comprising a cavity with an open end and a light barrier positioned in the cavity;

wherein the light barrier is facing towards the opening and forms a path between the light barrier and the opening.

10. The smoke detector of claim 9, wherein a free end of the light barrier is parallel with an end surface of the opening; a projection of the light barrier on the receiving space locates within the receiving space.

11. The smoke detector of claim 9, wherein an inner surface of the upper cover comprises a second terraced wall opposite to the first terraced wall.

12. The smoke detector of claim 11, wherein the upper cover comprises a cover plate and a flange extending from an edge of the cover plate, the flange is parallel to the first terraced wall.

13. The smoke detector of claim 11, wherein a peripheral surface of the flange is flush with an end surface of the opening.

14. The smoke detector of claim 9, wherein the upper cover comprises a zigzag structure in the cavity, the zigzag structure is facing towards the installation part for the light emitter.

15. The smoke detector of claim 9, wherein the smoke chamber further comprises a base plate and a fastener connected between the base plate and the smoke detecting housing, the fastener comprises a first light emitter bearing surface and a first light receiver bearing surface, the smoke detecting housing comprises a second light emitter bearing surface coupling with the first light emitter bearing surface and a second light receiver bearing surface coupling with the first light receiver bearing surface.

16. The smoke detector of claim 9, wherein the enclosure comprises a top plate and annular side wall with one end connected to the top plate, the annular side wall defines a plurality of smoke entrances connected to the path.

17. The smoke detector of claim 9, wherein the smoke detector further comprises a testing unit, an alarm unit and a operating unit in the enclosure.

18. The smoke detector of claim 17, wherein the testing unit comprises a flexible printed circuit board and testing members and a button electrically connected to the flexible printed circuit board; the alarm unit comprises a plurality of warning lights; the enclosure comprises a button hole and a plurality of light holes.

* * * * *